US00PP24282P2

(12) United States Plant Patent
Konst

(10) Patent No.: US PP24,282 P2
(45) Date of Patent: Mar. 4, 2014

(54) ***ALSTROEMERIA* PLANT NAMED 'KONCAVITO'**

(50) Latin Name: *Alstroemeria hybrida*
Varietal Denomination: Koncavito

(75) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 46 days.

(21) Appl. No.: 13/506,947

(22) Filed: May 25, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Annette Para
(74) *Attorney, Agent, or Firm* — C. A. Whealy

(57) ABSTRACT

A new and distinct cultivar of *Alstroemeria* plant named 'Koncavito', characterized by its compact and mounding plant habit; sturdy and strong plants; vigorous growth habit; freely branching habit; numerous red-colored flowers; and good garden performance.

2 Drawing Sheets

Botanical designation: *Alstroemeria hybrida.*
Cultivar denomination: 'KONCAVITO'.

BACKGROUND OF THE INVENTION

The present invention relates to a new and distinct cultivar of *Alstroemeria* plant, botanically known as *Alstroemeria hybrida*, typically grown as a potted garden *Alstroemeria*, and hereinafter referred to by the name 'Koncavito'.

The new *Alstroemeria* plant is a product of a planned breeding program conducted by the Inventor in Nieuwveen, The Netherlands. The objective of the breeding program is to create new compact potted garden *Alstroemeria* plants that flower early and freely with attractive leaf and flower coloration.

The new *Alstroemeria* plant originated from a cross-pollination made by the Inventor in Nieuwveen, The Netherlands on Aug. 13, 2007 of a proprietary *Alstroemeria hybrida* selection identified as code number 21206-15, not patented, as the female, or seed, parent with a proprietary *Alstroemeria hybrida* selection identified as code number 07-0-RD, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands on Sep. 15, 2008.

Asexual reproduction of the new *Alstroemeria* plant by in vitro rhizogenesis in a controlled greenhouse environment in Nieuwveen, The Netherlands since Oct. 12, 2009 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncavito'. These characteristics in combination distinguish 'Koncavito' as a new and distinct *Alstroemeria* plant:

1. Compact and mounding plant habit.
2. Sturdy and strong plants.
3. Vigorous growth habit.
4. Freely branching habit.
5. Numerous red-colored flowers.
6. Good garden performance.

Plants of the new *Alstroemeria* can be compared to plants of the female parent selection. Plants of the new *Alstroemeria* differ primarily from plants of the female parent selection in the following characteristics:

1. Plants of the new *Alstroemeria* are more compact than plants of the female parent selection.
2. Plants of the new *Alstroemeria* and the female parent selection differ in flower color as plants of the female parent selection have reddish pink-colored flowers.

Plants of the new *Alstroemeria* can be compared to plants of the male parent selection. Plants of the new *Alstroemeria* differ primarily from plants of the male parent selection in flower color.

Plants of the new *Alstroemeria* can be compared to plants of the *Alstroemeria hybrida* 'Koncajoli', disclosed in U.S. Plant Pat. No. 22,267. In side-by-side comparisons conducted in Nieuwveen, The Netherlands, plants of the new *Alstroemeria* differed from plants of 'Koncajoli' in the following characteristics:

1. Plants of the new *Alstroemeria* were more compact than plants of 'Koncajoli'.
2. Plants of the new *Alstroemeria* had smaller flowers than plants of 'Koncajoli'.
3. Plants of the new *Alstroemeria* and 'Koncajoli' differed in flower color as plants of 'Koncajoli' had light red-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Koncavito' grown in container.

The photograph on the second sheet is a close-up view of a typical flowering plant of 'Koncavito'.

DETAILED BOTANICAL DESCRIPTION

The aforementioned photographs and following observations and measurements describe plants of the new *Alstroemeria* grown during the spring in 19-cm containers in a glass-covered greenhouse in Nieuwveen, The Netherlands and under cultural practices typical of commercial potted *Alstroemeria* production. During the production of the plants, day temperatures ranged from 6° C. to 30° C. and night temperatures ranged from 6° C. to 16° C. Plants were 36 weeks old when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Koncavito'.

Parentage:

*Female, or seed, parent.*—Proprietary *Alstroemeria hybrida* selection identified as code number 21206-15, not patented.

*Male or pollen parent.*—Proprietary *Alstroemeria hybrida* selection identified as code number 07-0-RD, not patented.

Propagation:

*Type.*—In vitro rhizogenesis.

*Root description.*—Thick, fleshy; color, close to 159D.

*Rooting habit.*—Freely branching; dense.

*Rhizome description.*—Shape: Elongate; rounded. Length: About 7 cm. Diameter: About 1 cm. Texture: Smooth. Color: Close to 161D.

Plant description:

*Plant habit.*—Compact and mounded; freely branching habit, bushy appearance; sturdy and strong plants; vigorous growth habit.

*Plant height.*—About 15 cm.

*Plant diameter* (*area of spread*).—About 30 cm.

Stem description:

*Aspect.*—Upright and somewhat outwardly spreading.

*Internode length.*—About 0.2 cm to 1 cm.

*Strength.*—Strong, sturdy.

*Texture.*—Smooth, glabrous.

*Color.*—Close to 138B to 138C.

Foliage description:

*Arrangement.*—Alternate; below the peduncle, arranged in a single whorl; leaves sessile.

*Length.*—About 4 cm to 9.5 cm.

*Width.*—About 1.2 cm to 3.8 cm.

*Shape.*—Oblanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to 137A. Developing leaves, lower surface: Close to 138A. Fully expanded leaves, upper surface: Close to 137A; venation, close to 137A. Fully expanded leaves, lower surface: Close to 137B; venation, close to 135A.

Flower description:

*Flower type and habit.*—Single cup-shaped flowers arranged in compound umbels; flowers face upright to outwardly; freely flowering habit; about three to ten flowers per inflorescence; and about 40 to 70 flowers developing per plant.

*Natural flowering season.*—Flowering continuous from the late spring until the autumn in The Netherlands.

*Fragrance.*—None detected.

*Flower longevity on the plant.*—About one to three weeks; flowers not persistent.

*Flower longevity as a cut flower.*—About one to two weeks; flowers not persistent.

*Flower buds.*—Length: About 3 cm to 4 cm. Diameter: About 1.2 cm. Shape: Ovoid. Color: Close to 59A and 46A; venation, close to 139A.

*Umbel height.*—About 10.5 cm.

*Umbel diameter.*—About 12.5 cm.

*Flower diameter.*—About 4.7 cm.

*Flower depth* (*height*).—About 6.7 cm.

*Perianth.*—Arrangement: Six arranged in two whorls, each whorl with two lateral and one median segments. Size, inner perianth: Length, lateral segments: About 6.1 cm. Width, lateral segments: About 1.9 cm. Length, median segment: About 5.2 cm. Width, median segment: About 1.9 cm. Size, outer perianth: Length, lateral segments: About 5.1 cm. Width, lateral segments: About 2.9 cm. Length, median segment: About 5.4 cm. Width, median segment: About 2.8 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Cordate. Base, inner and outer perianths, lateral and median segments: Attenuate. Margin, inner perianth, lateral and median segments: Entire. Margin, outer perianth, lateral and median segments: Entire; towards the apex, crenate to dentate. Texture, inner and outer perianths, lateral and median segments: Smooth, glabrous. Color, inner perianth: When opening, lateral segments, upper surface: Towards the apex, close to 53A; mid-section, close to 53B and 160A; towards the base, close to 36B; stripes, close to 187A. When opening, median segments, upper surface: Towards the apex, close to 60A; towards the base, close to 59C; stripes, close to 187A. When opening, lateral and median segments, lower surface: Towards the apex, close to 46A; towards the base, close to 53B. Fully opened, lateral segments, upper surface: Towards the apex, close to 53A; mid-section, close to 53B and 160B; towards the base, close to 37A; stripes, close to 187A. Fully opened, median segment, upper surface: Apex and mid-section, close to 46B; towards the base, close to 42B; stripes, close to 187A. Fully opened, lateral segments, lower surface: Close to 46B; apex, close to 46A; stripes, close to 53A. Fully opened, median segments, lower surface: Close to 47A; apex, close to 46A; stripes, close to 53A. Color, outer perianth:

When opening, lateral and median segments, upper surface: Apex, close to 187B; mid-section, close to 46B; towards the base, close to 182C. When opening, lateral and median segments, lower surface: Apex, close to 137A; mid-section, close to 46A; towards the base, close to 182B. Fully opened, lateral and median segments, upper surface: Apex, close to 187A; mid-section, close to 53B; towards the base, close to 47A. Fully opened, lateral and median segments, lower surface: Apex, close to 137A; mid-section, close to 46B; towards the base, close to 46B.

*Pedicels.*—Length: About 9 mm. Diameter: About 2 mm. Strength: Strong. Angle: About 60° from vertical. Texture: Smooth, glabrous. Color: Close to 144A tinted with close to 187A.

*Reproductive organs.*—Stamens: Quantity per flower: Six. Anther shape: Oval. Anther size: About 3 mm by 5 mm. Anther color: Close to 183A. Pollen amount: Abundant. Pollen color: Close to 187A. Pistils: Quantity per flower: One. Pistil length: About 5.2 cm. Style length: About 2.4 cm. Style color: Close to 47A. Stigma color: Close to 46A. Ovary color: Close to 138A; venation, close to 183A.

*Fruits.*—Length: About 1.5 cm. Diameter: About 1.2 cm. Color: Close to 138B.

*Seeds.*—Seed production has not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncavito' as illustrated and described.

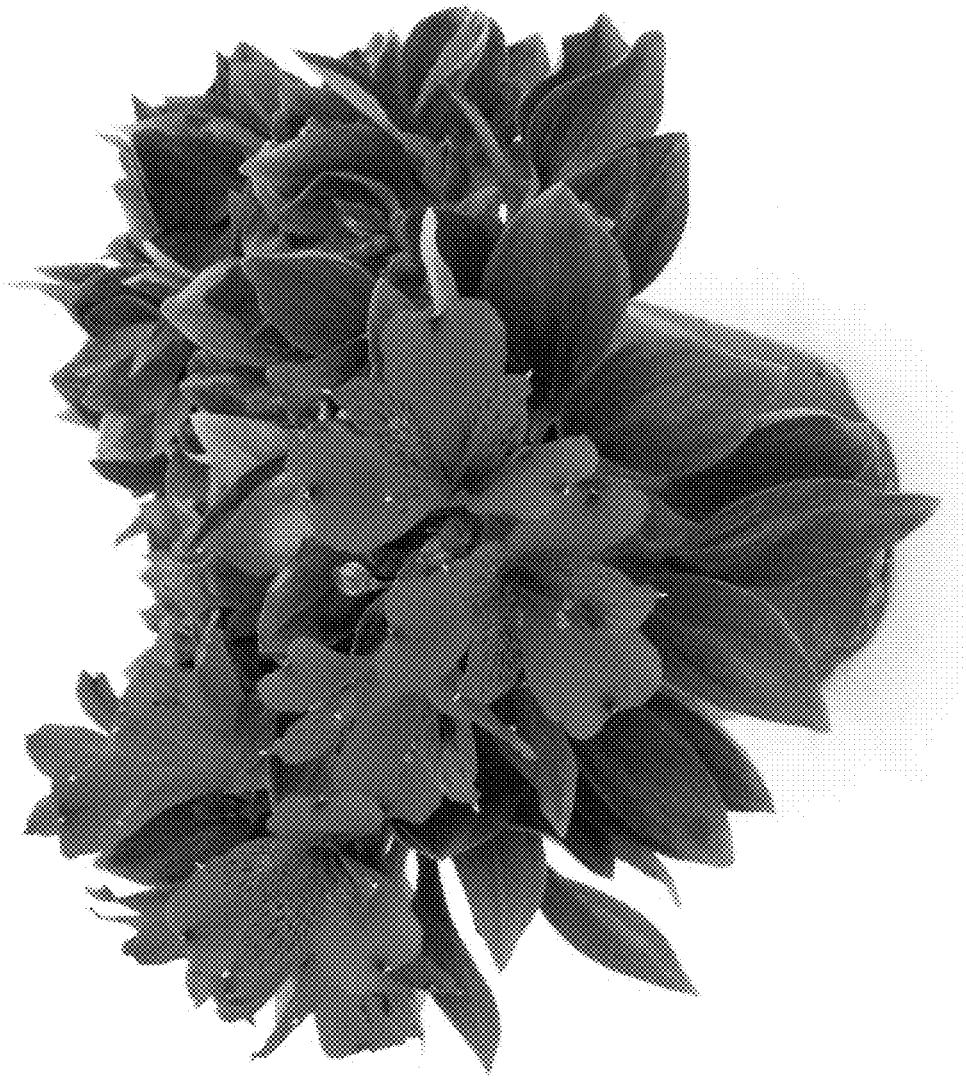

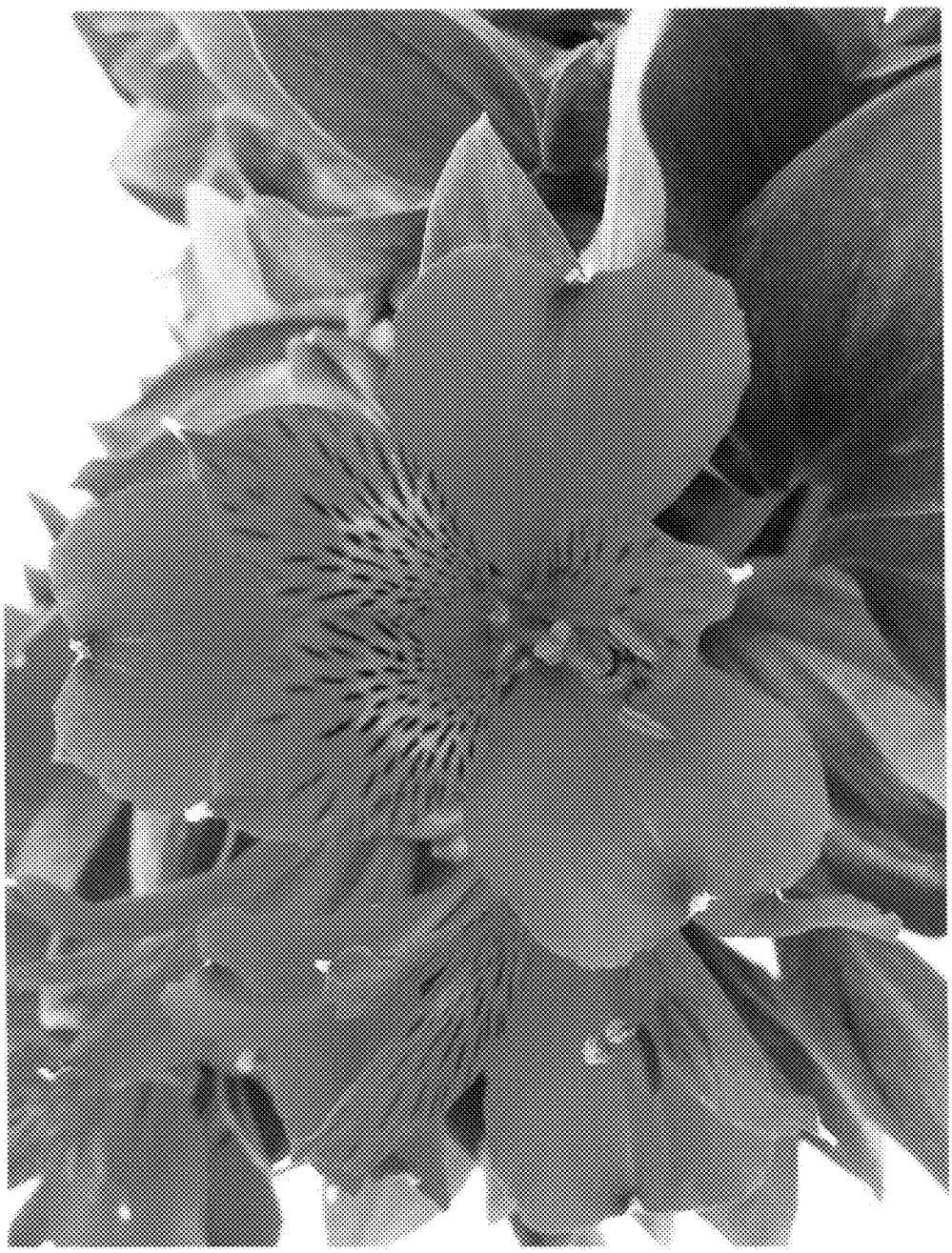

* * * * *